(12) United States Patent
Cheng et al.

(10) Patent No.: US 10,755,875 B2
(45) Date of Patent: Aug. 25, 2020

(54) ELECTRONIC SWITCH MECHANISM

(71) Applicant: Gyrus ACMI, Inc., Southborough, MA (US)

(72) Inventors: Ming J. Cheng, W. Warwick, RI (US); David C. Church, Millington, TN (US); Joseph Green, Bartlett, TN (US); Moussa Sane, Collierville, TN (US)

(73) Assignee: Gyrus ACMI, Inc., Southborough, MA (US)

( * ) Notice: Subject to any disclaimer, the term of this patent is extended or adjusted under 35 U.S.C. 154(b) by 0 days.

(21) Appl. No.: 16/089,491

(22) PCT Filed: Apr. 7, 2016

(86) PCT No.: PCT/US2016/026454
§ 371 (c)(1),
(2) Date: Sep. 28, 2018

(87) PCT Pub. No.: WO2017/176275
PCT Pub. Date: Oct. 12, 2017

(65) Prior Publication Data
US 2019/0115168 A1  Apr. 18, 2019

(51) Int. Cl.
| | |
|---|---|
| *H01H 13/18* | (2006.01) |
| *H01H 21/00* | (2006.01) |
| *A61B 17/00* | (2006.01) |
| *H01H 21/04* | (2006.01) |
| *A61B 18/00* | (2006.01) |

(52) U.S. Cl.
CPC .......... *H01H 13/186* (2013.01); *A61B 17/00* (2013.01); *H01H 21/00* (2013.01); *H01H 21/04* (2013.01); *A61B 2017/00367* (2013.01); *A61B 2017/00446* (2013.01); *A61B 2018/00178* (2013.01); *A61B 2018/00916* (2013.01); *A61B 2018/00952* (2013.01); *H01H 2221/016* (2013.01); *H01H 2300/014* (2013.01)

(58) Field of Classification Search
CPC .......................................... A61B 2018/00178; A61B 2018/00916; A61B 2017/00367; A61B 2017/00371; H01H 13/186; H01H 21/00; H01H 2300/014
See application file for complete search history.

(56) References Cited

U.S. PATENT DOCUMENTS

| | | | |
|---|---|---|---|
| 4,618,754 A | 10/1986 | Gross | 200/159 |
| 5,217,478 A * | 6/1993 | Rexroth | A61B 17/32002 606/172 |
| 5,376,765 A | 12/1994 | Holmes et al. | 200/344 |

(Continued)

FOREIGN PATENT DOCUMENTS

| | | |
|---|---|---|
| CN | 104349733 A | 2/2015 |
| EP | 2 594 218 A1 | 5/2013 |

(Continued)

*Primary Examiner* — Vanessa Girardi
(74) *Attorney, Agent, or Firm* — Harrington & Smith

(57) ABSTRACT

A switch mechanism includes a housing with a fenestration, a switch element held in the housing, and a first tab and a second tab each being pivotally attached to an opposite lateral edge of the fenestration. The tabs are constrained to rotational movement relative to the housing so that contact with the first tab or the second tab causes the respective tab to rotate to actuate the switch element.

11 Claims, 4 Drawing Sheets

(56) References Cited

U.S. PATENT DOCUMENTS

| | | | | |
|---|---|---|---|---|
| 5,601,601 | A | * | 2/1997 | Tal .......................... A61B 17/29 606/174 |
| 6,303,887 | B1 | | 10/2001 | Ando ............................. 200/512 |
| 6,880,989 | B2 | | 4/2005 | Sotome ........................ 396/502 |
| 6,911,608 | B2 | | 6/2005 | Levy ........................... 200/302.1 |
| 6,998,554 | B2 | | 2/2006 | Shimoda et al. ............. 200/341 |
| 8,699,741 | B2 | * | 4/2014 | Hestehave .......... H04M 1/6066 381/367 |
| 9,439,668 | B2 | * | 9/2016 | Timm ............ A61B 17/320068 |
| 9,907,565 | B2 | * | 3/2018 | Aldridge ........ A61B 17/320068 |
| 2004/0061059 | A1 | | 4/2004 | Gobel et al. .............. 250/370.01 |
| 2012/0123203 | A1 | | 5/2012 | Riva ............................. 600/104 |
| 2013/0138096 | A1 | | 5/2013 | Benn ............................... 606/33 |
| 2013/0140164 | A1 | | 6/2013 | Chen ............................ 200/5 A |
| 2015/0066026 | A1 | | 3/2015 | Hart et al. ...................... 606/46 |

FOREIGN PATENT DOCUMENTS

| | | |
|---|---|---|
| JP | H-6000193 A | 11/1994 |
| JP | 11111099 A | 4/1999 |
| JP | 2000048676 A | 2/2000 |
| JP | 2012519023 A | 8/2012 |
| JP | 2012-243406 A | 12/2012 |
| JP | 2013116323 A | 6/2013 |
| WO | WO 2013/154921 A2 | 10/2013 |

* cited by examiner

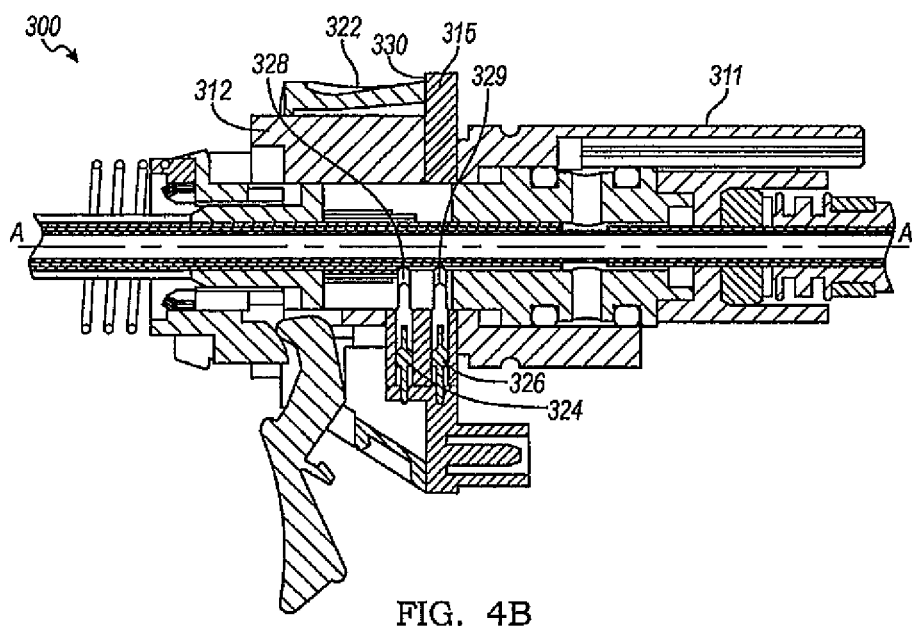
FIG. 4B
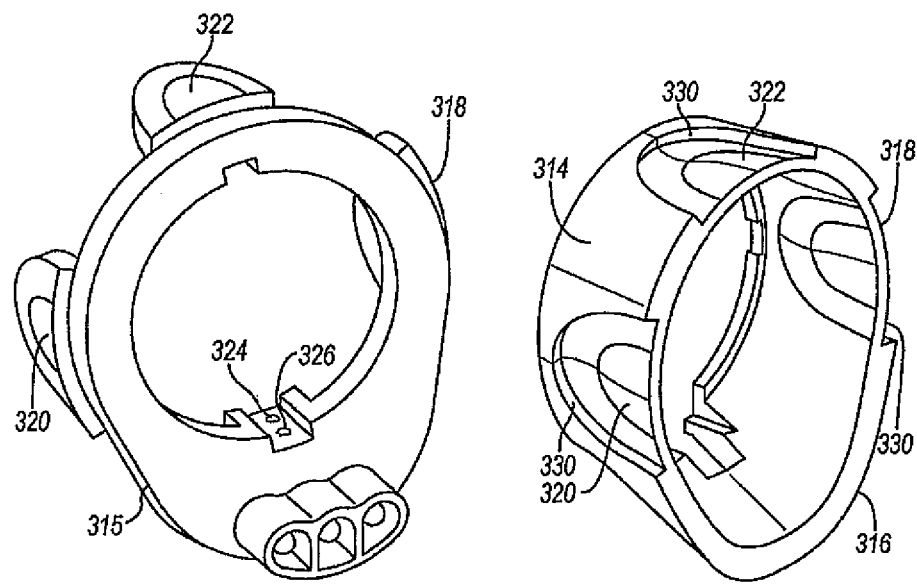
FIG. 4C
FIG. 4D

ELECTRONIC SWITCH MECHANISM

This patent application is a U.S. National Stage application of International Patent Application Number PCT/US2016/026454 filed Apr. 7, 2016, which is hereby incorporated by reference in its entirety.

FIELD

The present disclosure relates to an electronic switch mechanism. More specifically, the present disclosure relates to an electronic switch mechanism for an electrosurgical instrument.

BACKGROUND

The statements in this section merely provide background information related to the present disclosure and may or may not constitute prior art.

Typical switches for electrosurgical instruments, as well as other non-medical devices, include one or more tactile push buttons to activate the instrument. For example, certain instruments employ one button for a left-handed operator and a second button for a right-handed operator. Among the literature that can pertain to this technology include, for example, the following patent documents and published patent applications: U.S. Pat. Nos. 4,618,754; 5,376,765; 6,303,887; 6,880,989; 6,911,608; 6,998,554; and U.S. Patent Publication No. 2013/0140164, the entire contents of which are incorporated herein by reference for all purposes.

Accordingly, it would be desirable for an instrument to include a switch mechanism that accommodates ambidextrous operation of the instrument.

SUMMARY

The present disclosure provides an electronic switch mechanism. In various arrangements, the switch mechanism is associated with an electrosurgical instrument. The switch mechanism has two or more buttons or tabs to enable a medical practitioner to actuate the instrument. More specifically, the two or more buttons or tabs are configured to allow the medical practitioner to operate the instrument with either hand. That is, the medical practitioner can use his/her fingers or thumbs from either hand to provide ambidextrous operation of the instrument.

Accordingly, pursuant to one aspect of the present invention, a switch mechanism includes a housing with a fenestration, a switch element held in the housing, and a first tab and a second tab each being pivotally attached to an opposite lateral edge of the fenestration. The tabs are constrained to rotational movement relative to the housing so that contact with the first tab or the second tab causes the respective tab to rotate to actuate the switch element.

This aspect of the present invention can be further characterized by one or any combination of the features described herein, such as: a membrane positioned over the tabs to seal the fenestration; the housing has a centerline and the switch element is on the centerline; the first tab and the second tab extend towards the centerline without reaching each other; the first tab and the second tab are spaced apart equally from the centerline; at least one tab has a contact region over an arc span of about 30°; a rigid rocker pivotally constrained on the housing at a pivot point located between the first tab and the second tab; and the switch element is a dome switch so that contact with either the first tab or the second tab causes the respective tab to contact the rigid rocker which in turn contacts and actuates the dome switch.

Accordingly, pursuant to another aspect of the present invention, a switch mechanism includes a housing with a fenestration, a switch element held in the housing, the switch element being a dome switch, a first tab and a second tab, each being pivotally attached to an opposite lateral edge of the fenestration, and a rigid rocker pivotally constrained on the housing at a pivot point located between the first tab and the second tab. The tabs are constrained to rotational movement relative to the housing so that contact with the first tab or the second tab causes the respective tab to rotate and contact the rigid rocker which in turn contacts and actuates the dome switch.

The foregoing aspect of the present invention can be further characterized by one or any combination of the features described herein, such as: at least one membrane positioned over the tabs to seal the fenestration; the housing has a centerline and the switch element is on the centerline; and the first tab and the second tab extend towards the centerline without reaching each other.

Accordingly, pursuant to yet another aspect of the present invention, a switch mechanism includes a housing, a first switch element held in the housing, a second switch element held in the housing, a third switch element held in the housing, and a circuit board that electrically communicates with the first, second, and third switch elements. Contact with the first, second or third switch element actuates the respective switch element so that an electrical signal is transmitted from the switch element to the circuit board.

This aspect of the present invention can be further characterized by one or any combination of the features described herein, such as: the switch elements are membrane switch elements; each membrane switch element includes a flexible membrane; the flexible membranes are insert molded; the housing includes a first fenestration, a second fenestration and a third fenestration, each of the first, second and third switch elements being positioned in a respective fenestration; the housing has a longitudinal axis and the first, second and third switch elements are positioned about the longitudinal axis; and the first, second and third switch elements are spaced at 3 O'clock, 6 O'clock and 9 O'clock about the longitudinal axis.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

Figure 4A:
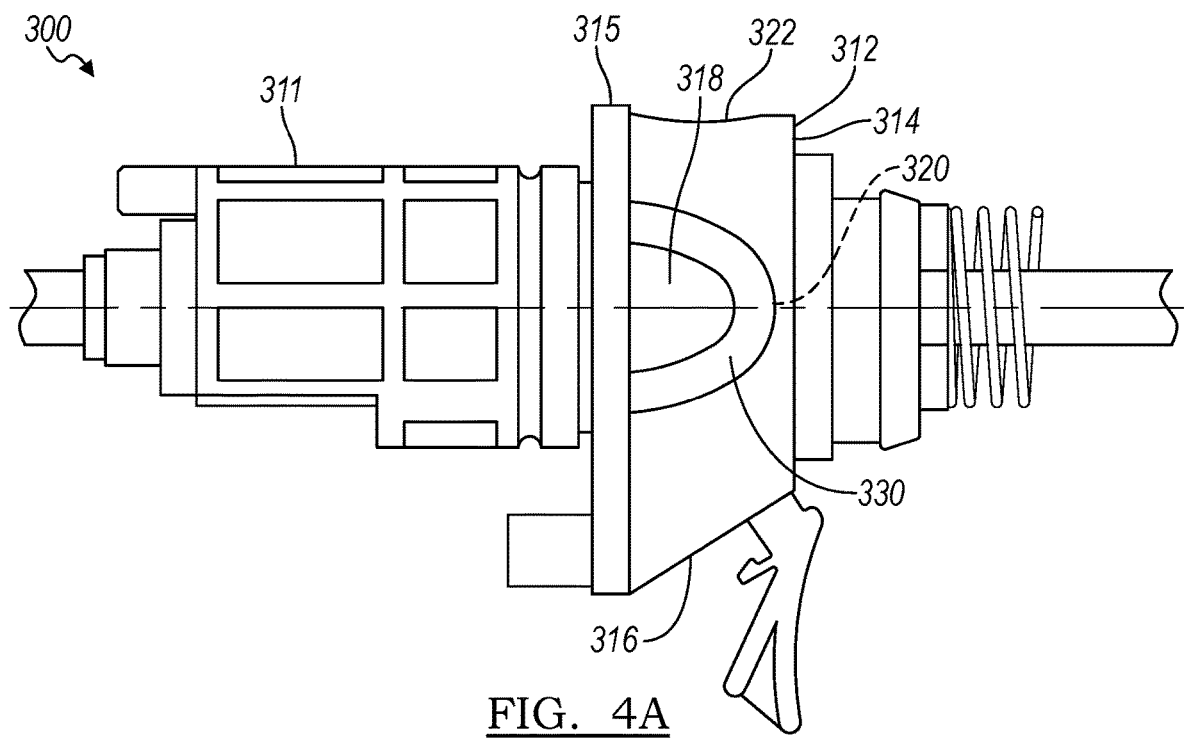
FIG. 4A is a side view of yet another alternative switch mechanism in accordance with the principles of the present invention.

FIG. 4B cross-section view of the switch mechanism shown in FIG. 4A;

FIG. 4C is a perspective view of a circuit board for the switch mechanism shown in FIG. 4A; and FIG. 4D is a perspective view of a housing for the switch mechanism shown in FIG. 4A.

DETAILED DESCRIPTION

The following description is merely exemplary in nature and is not intended to limit the present disclosure, application, or uses.

Figure 1A:
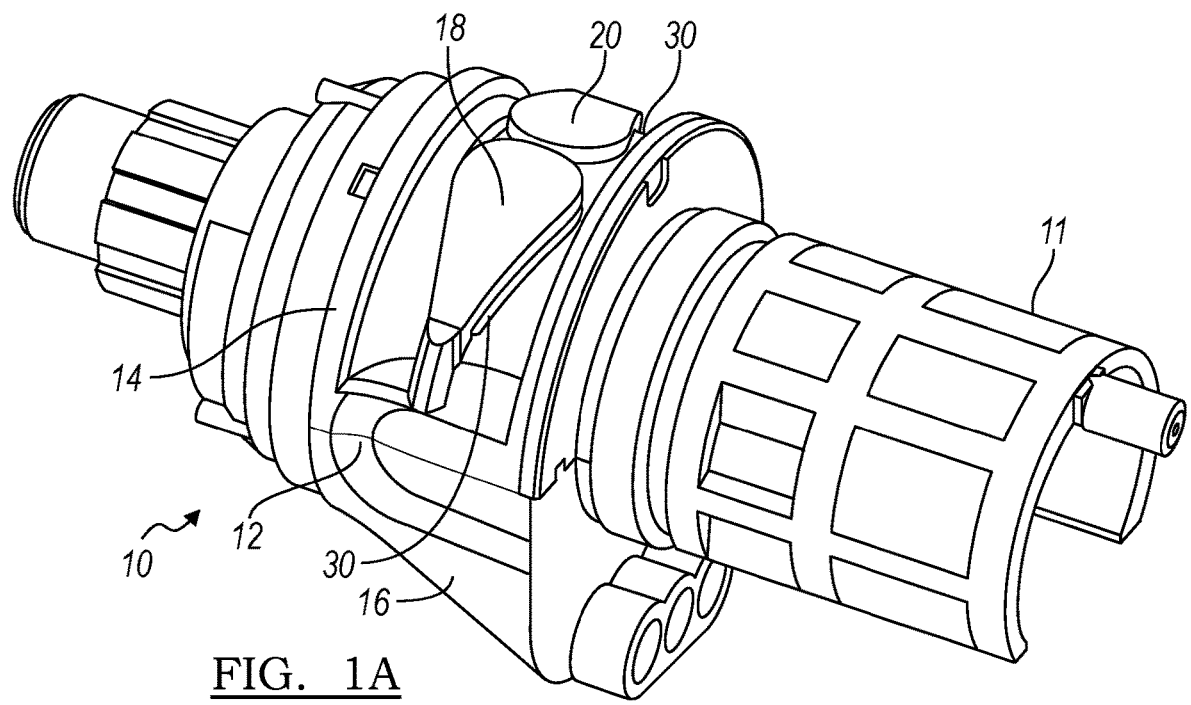
FIG. 1A is a perspective view of a switch mechanism in accordance with the principles of the present invention.
Figure 1B:
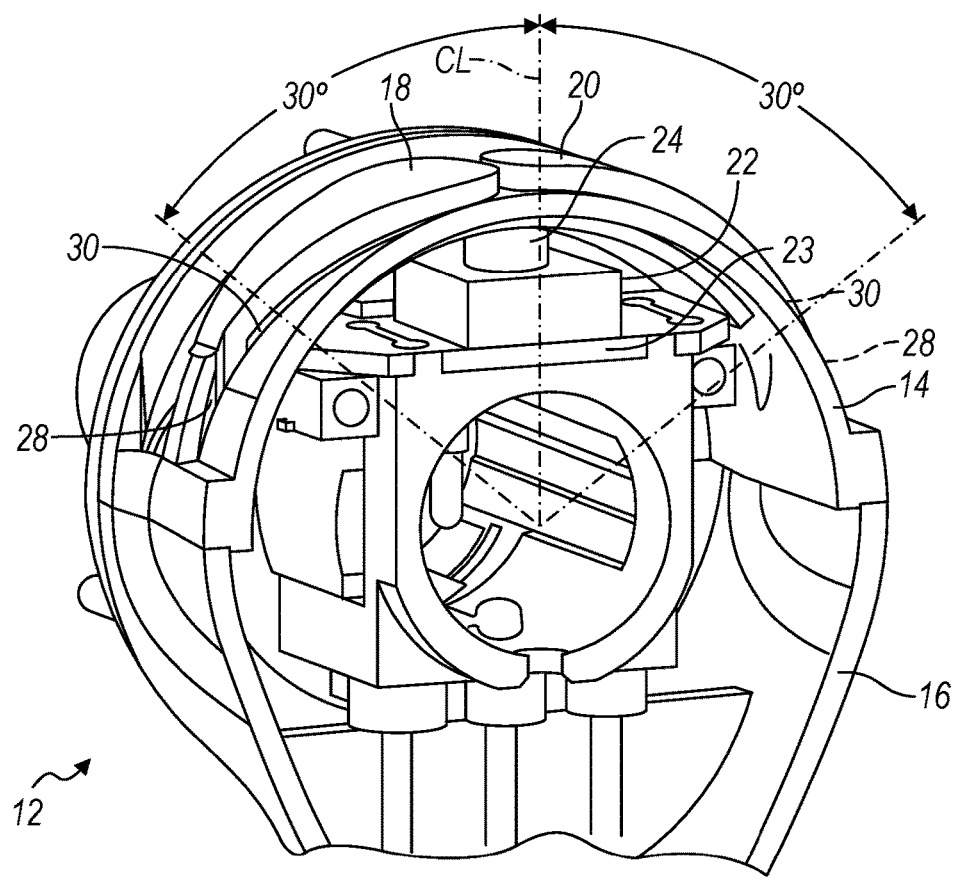
FIG. 1B is an interior view of the switch mechanism shown in FIG. 1A.

Referring now to FIGS. 1A and 1B, a portion of an electrosurgical instrument embodying the principles of the present invention is illustrated therein and designated at 10. The electrosurgical instrument includes an electronic switch mechanism 12 attached to a handle 11. The switch mechanism 12 and the handle 11 can be separate units or a single integral unit.

The electronic switch mechanism 12 includes an upper housing 14 and a lower housing 16. The upper housing 14 includes a pair of openings or fenestrations 30 that holds a first tab 18 and a second tab 20. The upper housing 14 and the lower housing 16 further includes a switch 22 supported on an internal structure, such as the interior platform 23, at the centerline, CL, of the switch mechanism 12, and each tab 18 and 20 is pivotally attached at a lateral most edge 28 of respective fenestrations 30. Accordingly, each tab 18 and 20 is constrained to rotational movement about the edge 28 relative to the upper housing 14 and the lower housing 16. Hence, when either tab 18, 20 is pressed, for example, by a medical professional, a medial portion of the respective tab contacts and presses against the button 24, which, in turn, actuates the switch 22.

The switch 22 in certain arrangements controls the activation of an energy source. For example, if the switch mechanism 12 is associated with an electrosurgical instrument with bipolar electrodes, the switch mechanism may control the operation of a radiofrequency (RF) energy source electrically connected to the instrument. Hence, when a medical profession presses either tab 18 or 20 to actuate the switch mechanism 12, electrical energy is delivered to the electrodes to treat, for example, tissue of a patient. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

The tabs 18 and 20 are arranged to enable a medical practitioner to press the tabs over an arc span of about 30° from the center line, CL. Accordingly, if a force is applied to either tab 18 or 20 over this 30° arc span, for example, with a finger or a thumb from either hand of the medical practitioner, the resulting displacement of the tab 18 or 20 is translated into rotational motion about the edge 28, which, in turn, produces translation motion of the button 24 to actuate the switch 22. Actuation of the switch 22 delivers an electrical signal form the switch mechanism 12 to operate the instrument associated with the switch mechanism 12. In other arrangements, the arc span can be greater or less than 30°.

Figure 2A:
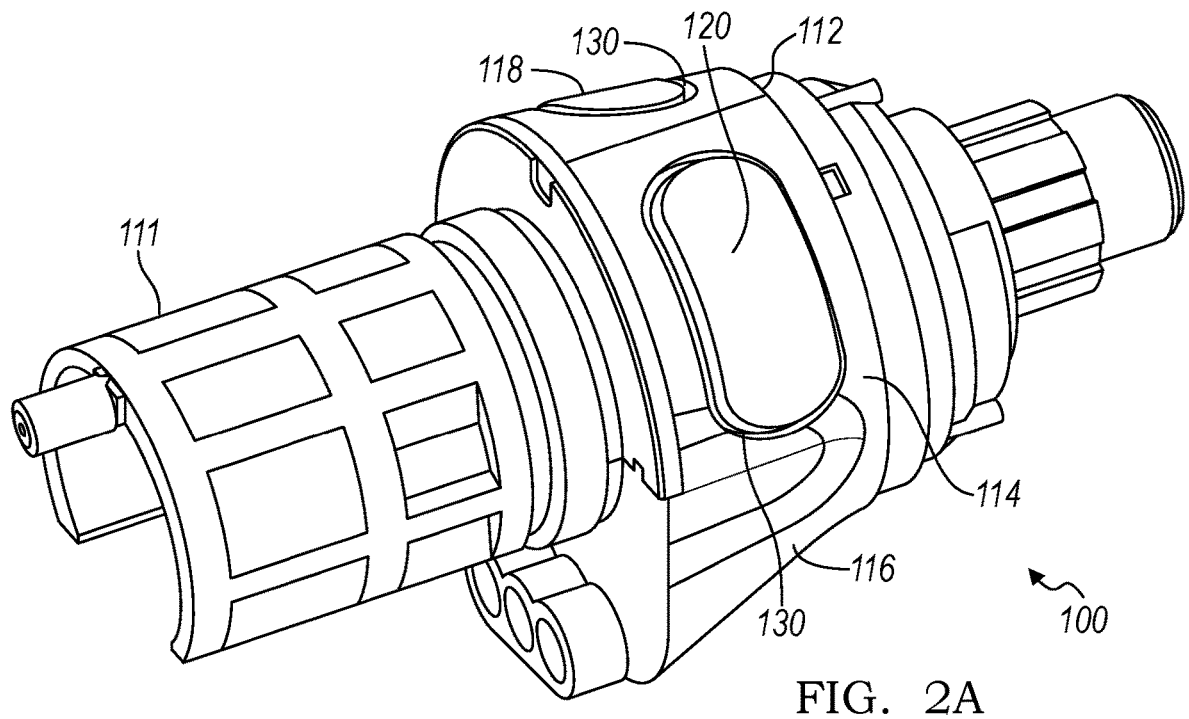
FIG. 2A is a perspective view of an alternative switch mechanism in accordance with the principles of the present invention.
Figure 2B:
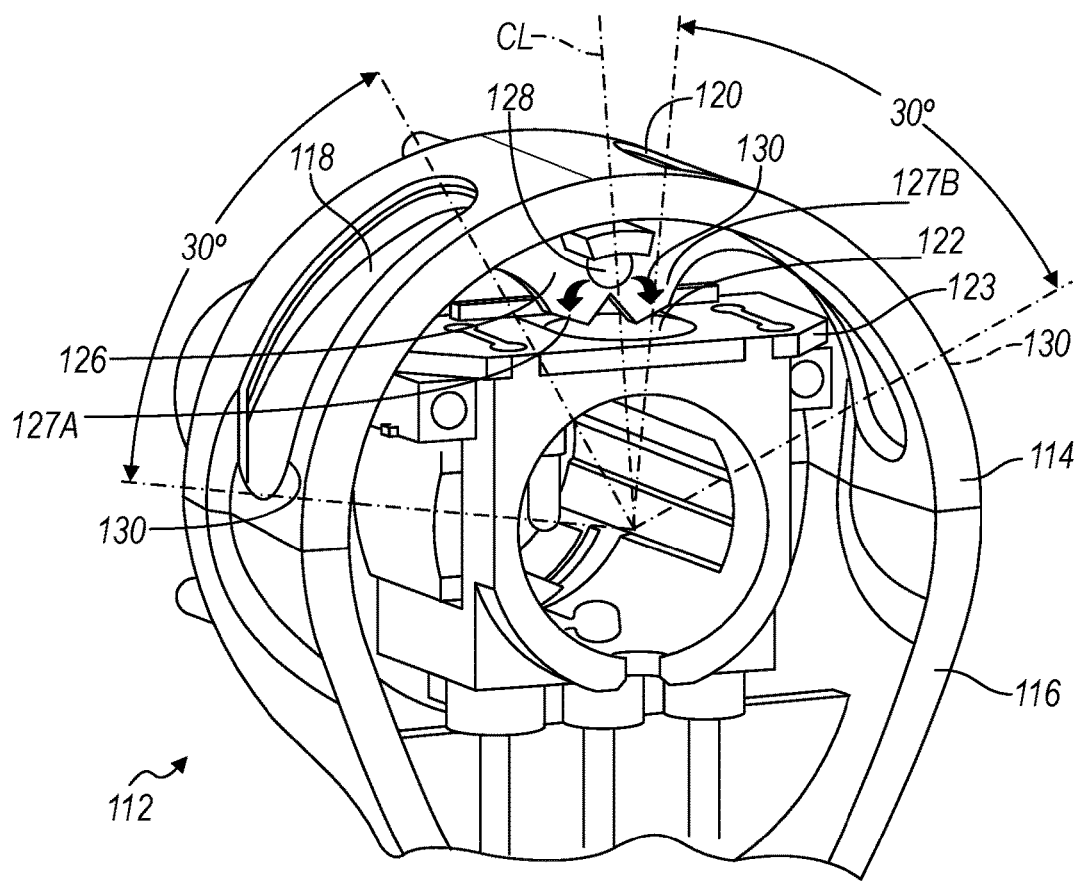
FIG. 2B is an interior view of the switch mechanism shown in FIG. 2A.

Turning now to FIGS. 2A and 2B, there is shown a portion of an alternative electrosurgical instrument 100 in accordance with the principles of the present invention. The electrosurgical instrument includes an electronic switch mechanism 112 attached to a handle 111. The switch mechanism 112 and the handle 111 can be separate units or a single integral unit.

The electronic switch mechanism 112 includes an upper housing 114 and a lower housing 116. The upper housing 114 includes a pair of openings or fenestrations 130 that holds a first tab 118 and a second tab 120. The first tab 118 and the second tab 120 are attached to a rigid rib member or rocker 126, and the rocker 126 is attached to the upper housing 114 on a rod 128 so that the rocker 126 pivots about the rod 128. The switch mechanism 112 further includes a switch 122 supported on an internal structure, such as the interior platform 123, at the centerline, CL, of the switch mechanism 112. In some arrangements, the first tab 118, the second tab 120, and the rocker 126 are a single integral unit.

In certain arrangements, the switch 122 can be a membrane switch or a dome switch as shown in FIG. 2B. Hence, when either tab 118, 120 is pressed, for example, by a medical professional, the rocker 126 pivots about the pivot point 128 as indicated by the arrows 130. The pivoting motion of the rocker 126, in turn, results in a projection 127A or 127B of the rocker 126 contacting the dome switch 122, which, in turn, actuates the switch 122. Specifically, if the tab 118 is pressed, the rocker 126 pivots counterclockwise so that the projection 127A contacts and actuates the switch 122. Similarly, if the tab 120 is pressed, the rocker 126 pivots clockwise so that the projection 127B contacts and actuates the switch 122.

The switch 122 can control the activation of an energy source. For example, if the switch mechanism 112 is associated with an electrosurgical instrument with bipolar electrodes, the switch mechanism may control the operation of a radiofrequency (RF) energy source electrically connected to the instrument. Hence, when a medical profession actuates the switch mechanism 112, electrical energy is delivered to the electrodes to treat, for example, tissue of a patient. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

The tabs 118 and 120 are arranged to enable a medical practitioner to press the tabs over an arc span of about 30°, as shown in FIG. 2B. Accordingly, if a force is applied to either tab 118 or 120 over this 30° arc span, for example, with a finger or a thumb from either hand of the medical practitioner, the resulting displacement of the tab 118 or 120 is translated into rotational motion of the rocker 126, which, in turn, contacts and actuates the dome switch 122. Actuation of the dome switch 122 delivers an electrical signal form the switch mechanism 112 to operate the instrument associated with the switch mechanism 112. In other arrangements, the arc span can be greater or less than 30°. Note also that the contact region is offset or spaced away from the centerline, CL. More specifically, there is a gap greater than 0° between the centerline, CL, and the inner edge of each tab 118, 120. In some specific arrangements, the gap is about 30°, while in other arrangements the gap is less than or greater than 30°.

Figure 3:
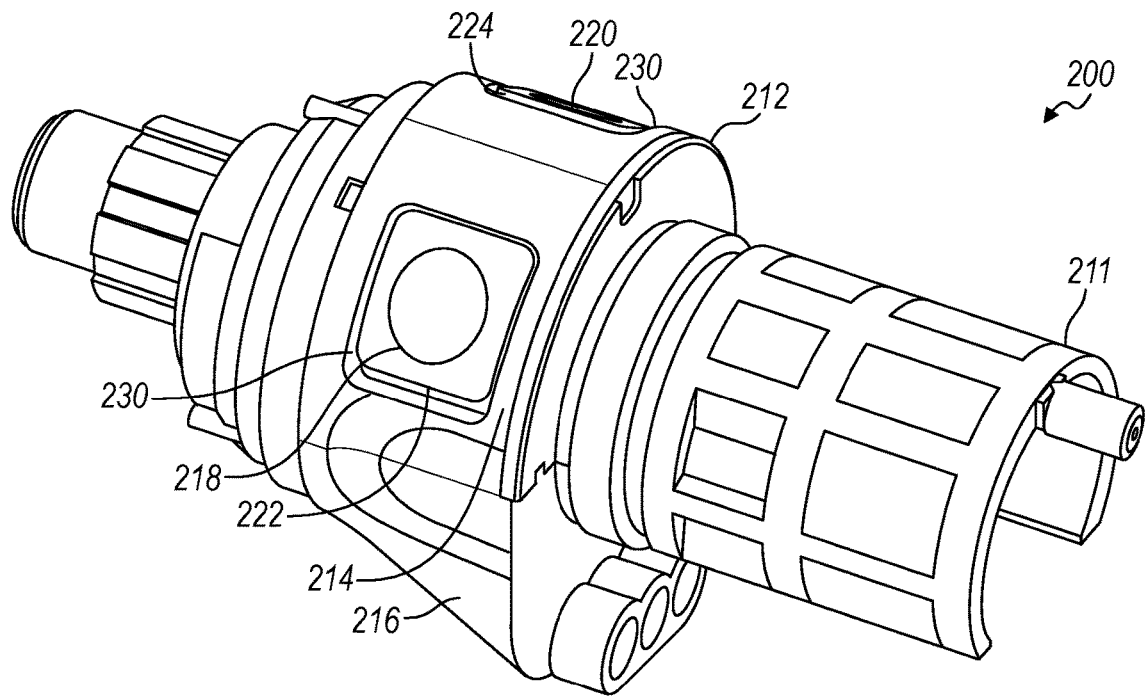
FIG. 3 is a perspective view of another alternative switch mechanism in accordance with the principles of the present invention.

Turning now to FIG. 3, there is shown a portion of an alternative electrosurgical instrument 200 in accordance with the principles of the present invention. The electrosurgical instrument includes an electronic switch mechanism 212 attached to a handle 211. The switch mechanism 212 and the handle 211 can be separate units or a single integral unit.

The electronic switch mechanism 212 includes an upper housing 214 and a lower housing 216. The upper housing 214 includes a pair of openings or fenestrations 230 that holds a first tab or button 218 and a second tab or button 220. Each tab or button 218, 220 is covered by a respective membrane 222, 224, and each tab or button 218, 220 can be an individual switch mechanism that selectively actuate the instrument 200. In particular, each tab or button 218, 220 can be an individual membrane switch that delivers an electrical signal to actuate the instrument 200.

The switch mechanism 212 in certain arrangements controls the activation of an energy source. For example, if the switch mechanism 212 is associated with an electrosurgical instrument with bipolar electrodes, the switch mechanism may control the operation of a radiofrequency (RF) energy source electrically connected to the instrument. Hence, when a medical profession actuates the switch mechanism 212, electrical energy is delivered to the electrodes to treat, for example, tissue of a patient. For example, if a force is applied to either button 218 or 220 with a finger or a thumb from either hand of the medical practitioner, the resulting displacement of the button 218 or 220 actuates the switch mechanism 212, which, in turn, delivers an electrical signal from the switch mechanism 212 to operate the instrument associated with the switch mechanism 212. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

Referring to FIGS. 4A-4D, there is shown yet another alternative electrosurgical instrument 300 in accordance with the principles of the present invention. The electrosurgical instrument includes an electronic switch mechanism 312 attached to a handle 311. The switch mechanism 312 and the handle 311 can be separate units or a single integral unit.

The electronic switch mechanism 312 includes an upper housing 314 and a lower housing 316. The upper housing 314 includes a set of openings or fenestrations 330 that holds a first tab or button 318, a second tab or button 320, and a third tab or button 322. Each tab or button 318, 320, 322 can be covered by a respective membrane similar to that described above with respect to the instrument 200. Each tab or button 318, 320, 322 can be individual switch mechanisms that selectively actuate the instrument 300. In particular, each tab or button 318, 320, 322 can be an individual membrane switch that delivers an electrical signal to actuate the instrument 300.

In the arrangement shown in FIGS. 4A-4D, the tabs or buttons 318, 320, 322 are associated with a circuit board 315. Hence, when any of the tabs or buttons 318, 320 or 322 is pressed, for example, by a medical professional, a signal is transmitted from contacts 328, 329 in the lower housing 316 to respective contacts 324, 326 in the circuit board 315, which in turn actuates the instrument 300. In a particular embodiment, the contacts 328 and 324 are associated with a bipolar operation of the instrument 300 while the contacts 329 and 326 are associated with a monopolar operation of the instrument 300.

As shown in FIGS. 4C and 4D, the buttons 318, 320, 322 are arranged at the 3 O'clock, 9 O'clock and 12 O'clock positions about the longitudinal axis, A, of the instrument 300. In other arrangements the buttons can be spaced closer together or further apart.

The switch mechanism 312 in certain arrangements controls the activation of an energy source. For example, if the switch mechanism 312 is associated with an electrosurgical instrument with bipolar electrodes, the switch mechanism may control the operation of a radiofrequency (RF) energy source electrically connected to the instrument. Hence, when a medical profession actuates the switch mechanism 312, electrical energy is delivered to the electrodes to treat, for example, tissue of a patient. Accordingly, if a force is applied to any of buttons 318, 320, 322, for example, with a fingers or a thumb from either hand of the medical practitioner, the resulting displacement of the button 318, 320, or 322 actuates the switch mechanism 312, which, in turn, delivers an electrical signal from the switch mechanism 312 to operate the instrument associated with the switch mechanism 312. The associated instrument can be forceps that coagulate or cut the tissue. The instrument can be a monopolar instrument that only requires one electrode that interacts with a neutral electrode, which is likewise connected to the body of a patient. Alternatively, the instrument can be a bipolar electrosurgical instrument with two electrodes (a distal electrode and a proximal electrode). A RF voltage with different potentials is applied to such bipolar instruments so that a current passes from one electrode to the other electrode through the tissue, thereby heating the tissue to coagulate or cut the tissue.

In some arrangements, the aforementioned membranes covering the tabs or buttons in the instruments 200 and 300 can be insert molded from a flexible low-durometer material. In all of the instruments described above, that is, the instruments 10, 100, 200 and 300, the tabs, buttons, or membranes 18, 20, 118, 120, 218, 220, 318, 320, 322 are configured to enable a medical practitioner the ability to operate the respective instrument with either hand.

The description of the invention is merely exemplary in nature and variations that do not depart from the gist of the invention are intended to be within the scope of the invention. Such variations are not to be regarded as a departure from the spirit and scope of the invention.

What is claimed is:
1. A switch mechanism comprising:
a housing, the housing having an opening;
a switch element held in the housing;
a first tab and a second tab; the first tab and the second tab each being pivotally attached to an opposite lateral edge of the opening; and a rigid rocker pivotally constrained on the housing at a pivot point located between the first tab and the second tab;

wherein the tabs are constrained to rotational movement relative to the housing so that contact with the first tab or the second tab causes the respective tab to rotate to actuate the switch element; and wherein the switch element is a dome switch so that contact with either the first tab or the second tab causes the respective tab to contact the rigid rocker which in turn pivots the rigid rocker which in turn contacts and actuates the dome switch.

2. The switch mechanism of claim 1 further comprising a membrane positioned over the tabs to seal the opening.

3. The switch mechanism of claim 1 wherein at least one tab has a contact region over an arc span of about 30°.

4. The switch mechanism of claim 1 further comprising a rod attached to the housing between the switch element and an inner surface of the housing to pivotally constrain the rigid rocker.

5. The switch mechanism of claim 1 wherein the housing has a centerline and the switch element is on the centerline.

6. The switch mechanism of claim 5 wherein the first tab and the second tab extend towards the centerline without reaching each other.

7. The switch mechanism of claim 5 wherein the first tab and the second tab are spaced apart equally from the centerline.

8. A switch mechanism comprising:

a housing, the housing having an opening;

a switch element held in the housing, the switch element being a dome switch;

a first tab and a second tab, the first tab and the second tab each being pivotally attached to an opposite lateral edge of the opening, and a rigid rocker pivotally constrained on the housing at a pivot point located between the first tab and the second tab, wherein the tabs are constrained to rotational movement relative to the housing so that contact with the first tab or the second tab causes the respective tab to rotate and contact the rigid rocker which in turn contacts and actuates the dome switch.

9. The switch mechanism of claim 8 further comprising at least one membrane positioned over the tabs to seal the opening.

10. The switch mechanism of claim 8 wherein the housing has a centerline and the switch element is on the centerline.

11. The switch mechanism of claim 10 wherein the first tab and the second tab extend towards the centerline without reaching each other.

* * * * *